US009617668B2

(12) United States Patent
Chatterjee et al.

(10) Patent No.: US 9,617,668 B2
(45) Date of Patent: Apr. 11, 2017

(54) NONWOVEN WEBS AND MULTI-COMPONENT FIBERS COMPRISING A POLYDIORGANOSILOXANE POLYAMIDE AND METHODS OF MELT BLOWING

(75) Inventors: Joon Chatterjee, Bloomington, MN (US); Donald R. Battles, Arden Hills, MN (US); Matthew T. Scholz, Woodbury, MN (US); David S. Hays, Woodbury, MN (US); Bradley W. Eaton, Woodbury, MN (US); Torrence B. Stahl, White Bear Lake, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 349 days.

(21) Appl. No.: 14/233,174

(22) PCT Filed: Aug. 8, 2012

(86) PCT No.: PCT/US2012/049900
§ 371 (c)(1),
(2), (4) Date: Jan. 16, 2014

(87) PCT Pub. No.: WO2013/022913
PCT Pub. Date: Feb. 14, 2013

(65) Prior Publication Data
US 2014/0163446 A1 Jun. 12, 2014

(51) Int. Cl.
*D04H 3/005* (2012.01)
*A61F 13/00* (2006.01)
*D01D 5/098* (2006.01)
*D01F 8/10* (2006.01)
*B32B 5/02* (2006.01)
*D01F 6/78* (2006.01)
*D01F 6/80* (2006.01)
*D01F 8/16* (2006.01)
*A61F 13/02* (2006.01)

(52) U.S. Cl.
CPC ....... *D04H 3/005* (2013.01); *A61F 13/00063* (2013.01); *A61F 13/0206* (2013.01); *A61F 13/0223* (2013.01); *A61F 13/0226* (2013.01); *A61F 13/0246* (2013.01); *B32B 5/022* (2013.01); *D01D 5/0985* (2013.01); *D01F 6/78* (2013.01); *D01F 6/80* (2013.01); *D01F 8/10* (2013.01); *D01F 8/16* (2013.01); *B32B 2262/12* (2013.01); *B32B 2556/00* (2013.01); *Y10T 428/2929* (2015.01); *Y10T 442/641* (2015.04)

(58) Field of Classification Search
CPC ...... C09J 7/0246; C09J 183/10; C09J 123/06; C09J 123/08; C09J 2483/00; B32B 7/12; B32B 27/283; B32B 2307/56; B32B 5/022; B32B 2262/12; B32B 2556/00; B32B 3/00; C09D 123/08; C09D 123/06; C08L 23/08; C08L 23/06; C08L 83/10; C08L 2207/066; C08L 2205/06; C08L 2203/16; C08L 2201/08; C08L 2205/03; C08L 83/14; C08G 77/455; C08G 69/00; C08G 77/54; C08G 77/388; Y10T 428/31663; Y10T 428/24983; Y10T 428/2852; Y10T 428/2929; Y10T 422/641; Y10T 428/1397; Y10T 428/2982; Y10T 428/24479; D04H 3/005; D01D 5/0985; D01F 8/10; D01F 6/78; D01F 6/80; D01F 8/16; A61F 13/00063; A61F 13/02; B29C 45/0001; C23C 14/12; Y10S 526/935
USPC ............ 602/45, 48; 264/510; 428/373, 447, 428/446; 442/364
See application file for complete search history.

(56) References Cited

U.S. PATENT DOCUMENTS

| 2,676,182 | A | 4/1954 | Daudt |
| 2,736,721 | A | 2/1956 | Dexter |
| 3,627,851 | A | 12/1971 | Brady |
| 3,772,247 | A | 11/1973 | Flannigan |
| 3,849,241 | A | 11/1974 | Butin |
| 4,935,484 | A | 6/1990 | Wolfgruber |
| 5,082,706 | A | 1/1992 | Tangney |
| 5,110,890 | A | 5/1992 | Butler |
| 5,214,119 | A | 5/1993 | Leir |
| 5,238,733 | A | 8/1993 | Joseph |
| 5,248,739 | A | 9/1993 | Schmidt |
| 5,319,040 | A | 6/1994 | Wengrovius |
| 5,461,134 | A | 10/1995 | Leir |
| 5,512,650 | A | 4/1996 | Leir |
| 6,007,914 | A | 12/1999 | Joseph |
| 6,083,856 | A | 7/2000 | Joseph |
| 6,107,222 | A * | 8/2000 | Joseph ................ C08F 290/148 428/449 |
| 6,171,985 | B1 | 1/2001 | Joseph |

(Continued)

FOREIGN PATENT DOCUMENTS

| CA | 2100865 | 4/1993 |
| EP | 1462547 | 1/2014 |
| JP | 63262604 A * | 10/1988 |
| JP | 2-36234 | 2/1990 |
| JP | 07-109443 | 4/1995 |
| JP | 2008-238493 | 10/2008 |
| WO | WO 9428054 A1 * | 12/1994 ............ C08G 77/42 |
| WO | WO 99-28402 | 10/1998 |

OTHER PUBLICATIONS

Abstract of JP 63-262604, Matsumoto et al., Oct. 28, 1988, 2 pages.*
Supplementary European Search Report; EP App. No. EP 12 82 1782; Feb. 27, 2015, 3 pgs.
Encyclopedia of Polymer Science and Engineering—Scattering to Structural Foams, vol. 15; John Wiley & Sons, New York (1989), pp. 265-270.
International Search Report PCT/US2012/49900 Oct. 18, 2012; 3 pgs.

*Primary Examiner* — Hai Vo

(57) ABSTRACT

The present invention pertains to nonwoven webs, and multi-component fibers comprising polydiorganosiloxane polyamide as well as method of making microfibers and multi-component fibers comprising a polydiorganosiloxane polyamide copolymer.

20 Claims, No Drawings

(56) References Cited

U.S. PATENT DOCUMENTS

| | | |
|---|---|---|
| 6,198,016 B1 | 3/2001 | Lucast |
| 6,224,898 B1 | 5/2001 | Balogh |
| 6,355,759 B1 | 3/2002 | Sherman |
| 6,368,687 B1 | 4/2002 | Joseph |
| 6,576,576 B1 | 6/2003 | Wang |
| 6,579,906 B2 | 6/2003 | Cooper |
| 7,371,464 B2 | 5/2008 | Sherman |
| 7,501,184 B2 | 3/2009 | Leir |
| 7,947,376 B2 | 5/2011 | Sherman |
| 2004/0156807 A1 | 8/2004 | Lin |
| 2006/0034899 A1 | 2/2006 | Ylitalo |
| 2007/0148475 A1* | 6/2007 | Sherman ............ C08G 69/42 428/447 |
| 2008/0318058 A1 | 12/2008 | Sherman |
| 2008/0318065 A1* | 12/2008 | Sherman ............ C09J 7/0246 428/446 |
| 2010/0121304 A1 | 5/2010 | Zhou |

FOREIGN PATENT DOCUMENTS

| | | |
|---|---|---|
| WO | 99/27880 | 6/1999 |
| WO | 99/28539 | 6/1999 |
| WO | 99/28540 | 6/1999 |
| WO | WO 99/27880 | 6/1999 |
| WO | WO 99/28539 | 6/1999 |
| WO | WO 99/28540 | 6/1999 |
| WO | 99/40952 | 8/1999 |
| WO | WO 99/40952 | 8/1999 |
| WO | WO 02/16682 | 2/2002 |
| WO | 02/090628 | 11/2002 |
| WO | WO 02/090628 | 11/2002 |
| WO | 2008/76391 | 6/2008 |
| WO | WO 2008/076391 | 6/2008 |
| WO | WO 2008/088730 | 7/2008 |
| WO | WO 2009-002611 | 12/2008 |
| WO | WO 2009-002668 | 12/2008 |

* cited by examiner

NONWOVEN WEBS AND MULTI-COMPONENT FIBERS COMPRISING A POLYDIORGANOSILOXANE POLYAMIDE AND METHODS OF MELT BLOWING

SUMMARY

In one embodiment, a multi-component fiber is described comprising a core and outer layer. At least a portion of the outer layer comprises a melt processable composition comprising a polydiorganosiloxane polyamide copolymer. At least a portion of the multi-component fiber core comprises a second melt processable polymer that does not comprise a polydiorganosiloxane polymer.

In another embodiment, a method of making microfibers is described comprising providing a composition comprising a polydiorganosiloxane polyamide copolymer wherein the composition has a complex viscosity ranging from 500 to 5000 poise at a temperature ranging from 200° C. to 300° C. and a shear rate of 1 hertz; and melt-blowing the composition to form a fibrous web. Such microfibers may optionally comprise a second melt processable polymer.

In another embodiment, a method of making multi-component microfibers is described comprising providing a first melt processable composition comprising a polydiorganosiloxane polyamide copolymer wherein the composition has a complex viscosity ranging from 500 to 5000 poise at a temperature ranging from 200° C. to 300° C. and a shear rate of 1 hertz; and providing a second melt processable composition that does not comprise a polydiorganosiloxane polymer; and melt-blowing the first and second melt processable compositions to form multi-component fibers.

In other embodiments, nonwoven webs and medical articles comprising (e.g. pressure sensitive) nonwoven webs are described. The nonwoven webs comprise the multi-component fiber and/or are prepared by the method described herein.

DETAILED DESCRIPTION OF PREFERRED EMBODIMENTS

The terms "polymer" and "polymeric material" refer to both materials prepared from one monomer such as a homopolymer or to materials prepared from two or more monomers such as a copolymer, terpolymer, or the like. "Polymer" also may refer to polymers that have been chemically modified post polymerization such as by grafting and the like. Likewise, the term "polymerize" refers to the process of making a polymeric material that can be a homopolymer, copolymer, terpolymer, or the like. The terms "copolymer" and "copolymeric material" refer to a polymeric material prepared from at least two monomers.

The term "polydiorganosiloxane" refers to a polymer comprising a divalent segment of formula

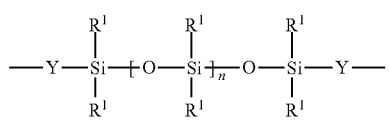

where each $R^1$ is independently an alkyl, haloalkyl, aralkyl, alkenyl, aryl, or aryl substituted with an alkyl, alkoxy, or halo; each Y is independently an alkylene, aralkylene, or a combination thereof; and subscript n is independently an integer of 40 to 1500. In some embodiments, the polydiorganosiloxane comprises divalent segments in combination with higher valency (e.g. branched) segments such as trivalent or tetravalent segments.

The term "adjacent" means that a first layer is positioned near a second layer. The first layer can contact the second layer or can be separated from the second layer by one or more additional layers.

The terms "room temperature" and "ambient temperature" are used interchangeably to mean a temperature in the range of 20° C. to 25° C.

Unless otherwise indicated, all numbers expressing feature sizes, amounts, and physical properties used in the specification and claims are to be understood as being modified in all instances by the term "about" Accordingly, unless indicated to the contrary, the numbers set forth are approximations that can vary depending upon the desired properties using the teachings disclosed herein.

The present invention is directed to fibers comprising a polydiorganosiloxane polyamide. The invention will be described herein with respect to a preferred polydiorganosiloxane polyamide, i.e. a polydiorganosiloxane polyoxamide. Such fibers typically have an average diameter of no greater than about 100 µm, and are useful in making nonwoven webs that can be used in making a wide variety of products. Preferably, such fibers have an average diameter of no greater than about 50 µm. Fibers of no greater than about 50 µm are often referred to as "microfibers." In some embodiments, the microfibers have an average fiber diameter of no greater than 40 µm, or 30 µm or 25 µm. In some embodiments, the microfibers have an average diameter of at least 5 µm or 10 µm.

Polydiorganosiloxane polyoxamide copolymers are advantageous because they can possess one or more of the following properties: resistance to ultraviolet light; good thermal and oxidative stability; good permeability to many gases; low surface energy; low index of refraction; low glass transition temperature; good hydrophobicity; good dielectric properties; good biocompatibility; good adhesive properties (either at room temperature or in the melt state). Fibers made of such polymers, and nonwoven webs of such fibers, are particularly desirable because they provide a material with a high surface area. The nonwoven webs also have high porosity. Nonwoven webs having a high surface area and porosity are desirable because they possess the characteristics of breathability, moisture transmission, conformability, and good adhesion to irregular surfaces.

Polydiorganosiloxane polyoxamide copolymers are favored over polydiorganosilane polyurea copolymers because of higher thermal stability which can be particularly important for blown microfiber processing. Polydiorganosiloxane polyoxamide copolymers can also be favored over polyacrylate and styrene-isoprene-styrene (SIS) and styrene-butadiene-styrene (SBS) type block copolymers for adhesion to skin applications. For example polydiorganosiloxane polyoxamide based pressure sensitive adhesives can exhibit excellent adhesion with very low trauma removal. Furthermore, lower adhesion to hair can reduces pain upon removal.

In some favored embodiments, the nonwoven webs described herein generally exhibit pressure-sensitive adhesive (PSA) properties at room temperature. The pressure-sensitive adhesive properties are typically a result of the incorporation of sufficient tackifier into the polydiorganosiloxane polyamide composition of at least the outer layer of the fibers. Nonwoven webs described herein typically exhibit (e.g. an initial) 90 degree peel strength to polypropylene of at least about 50, 75, or 100 grams per 2.54 centimeter width as measured by ASTM D3330-87. The (e.g. initial) peel strength is typically no greater than 500 grams per 2.54 centimeter. In some embodiments, the (e.g. initial) peel strength is no greater than 450, or 400, or 350, or 300 grams per 2.54 centimeter.

Nonwoven webs described herein can exhibit a shear adhesion holding power is at least 1,000, or 5,000, or 10,000 minutes for 500 g at room temperature, as measured according to the test method described in the examples. In order to obtain nonwoven pressure sensitive adhesive webs having such high shear adhesion holding power, it is preferred that the nonwoven comprises a single-layer fiber comprised of polydiorganosiloxane polyamide pressure sensitive adhesive or a multi-layered fiber wherein the weight ratio of polydiorganosiloxane polyamide pressure sensitive adhesive outer layer to second melt processable core layer is typically greater than 60/40, or 65/35, or 70/30. Hence, nonwoven webs comprising relatively high concentrations of polydiorganosiloxane polyamide pressure sensitive adhesive can be preferred, especially relative to nonwoven webs comprised of hot melt acrylate PSA's (such as described in U.S. Pat. No. 6,083,856).

Nonwoven webs comprising relatively high concentrations of polydiorganosiloxane polyoxamide pressure sensitive adhesive have also been found to exhibit lower adhesion build over time. In this embodiments, it is preferred that the nonwoven comprises a single-layer fiber comprised of polydiorganosiloxane polyoxamide pressure sensitive adhesive or a multi-layered fiber wherein the weight ratio of polydiorganosiloxane polyoxamide pressure sensitive adhesive outer layer to second melt processable core layer is typically greater than 50/50, or 55/45, or 60/40. As the concentration of polydiorganosiloxane polyoxamide pressure sensitive adhesive outer layer increases, the adhesion build tends to decrease. Hence in some embodiments, the weight ratio of polydiorganosiloxane polyoxamide pressure sensitive adhesive outer layer to second melt processable core layer is at least 65/35, or 70/30, or 75/25, or 80/20, or 85/15, or 90/10, or 95/05.

In some embodiments, wherein high shear adhesion holding power is not necessary, such as "temporary" uses, relatively low concentrations of polydiorganosiloxane polyoxamide pressure sensitive adhesive may be preferred in order to minimize cost. In these applications the nonwoven comprises a multi-layered fiber wherein the weight ratio of polydiorganosiloxane polyoxamide pressure sensitive adhesive outer layer to second melt processable core layer is typically less than 60/40, or 55/45, 50/50, or 45/55, or 40/60, or 35/65, or 30/70. In such embodiments, the shear adhesion holding power may be substantially lower than 1000 minutes (e.g. about 30 to 500 minutes).

Suitable polydiorganosiloxane polyamide (e.g. pressure sensitive adhesive) compositions are those that are capable of being extruded and forming fibers in a melt process, such as a spunbond process or a melt-blown process, without substantial degradation or gelling. The polydiorganosiloxane polyamides, as well as adhesives comprising such, can be heated to a temperature up to 200° C., up to 225° C., up to 250° C., up to 275° C., or up to 300° C. without noticeable degradation of the material. For example, when heated in a thermogravimetric analyzer in the presence of air, the copolymers or adhesives often have less than a 10 percent weight loss when scanned at a rate 50° C. per minute in the range of 20° C. to about 350° C. Alternatively, the copolymers or adhesive can often be heated at a temperature such as 250° C. for 1 hour in air without apparent degradation as determined by no detectable loss of physical properties (e.g. shear, peel)

Suitable (e.g. pressure sensitive adhesive) polydiorganosiloxane polyamide compositions have a sufficiently low viscosity in the melt such that they can be readily extruded. In some embodiments, the polydiorganosiloxane polyamide copolymer has a relatively high viscosity. However, the inclusion of tackifer reduces the viscosity of the polydiorganosiloxane polyamide such that the pressure sensitive adhesive composition has a sufficiently low viscosity to extrude. The polydiorganosiloxane polyamide (e.g. pressure sensitive adhesive) composition preferably has a complex viscosity at a temperature in a range from about 200° C. to 300° C. (i.e. at the melt blowing temperature) of at least about 500 poise and typically no greater than 5000 poise at a shear rate of 1 hertz as measured by the test method described in the examples. Without intending to be bound by theory, it is surmised that the actual viscosity (i.e. "apparent viscosity") during melt blowing is lower than the complex viscosity at 1 hertz due to the high shear forces of the melt blowing process. In some embodiments, the complex viscosity is no greater than 4500 poise, or 4000 poise, or 3500 poise at a temperature in a range from about 200° C. to 300° C. and a shear rate of 1 hertz. In some embodiments, the complex viscosity of the polydiorganosiloxane polyamide (e.g. pressure sensitive adhesive) composition at a temperature in a range from about 200° C. to 300° C. and a shear rate of 1 hertz is at least 1,000 poise, or 1500 poise, or 2000 poise. In favored embodiments, the composition has such apparent viscosity at a temperature no greater than 290° C., or 280° C., or 270° C., or 260° C., or 250° C., or 250° C. This allows the polydiorganosiloxane polyamide composition to be melt blown at lower temperatures, which is amendable to reducing degradation, particularly of a second melt processable polymer of a multi-component fiber.

In some embodiments, the polydiorganosiloxane polyamide (e.g. pressure sensitive adhesive) composition are capable of forming a melt stream in a melt blown process that maintains its integrity with few, if any, breaks in the melt stream. Hence, such PSA's have an extensional viscosity that allows them to be drawn effectively into fibers. In other embodiments, the second polymer (e.g. within the core) of a multi-component fiber contributes the desired extensional viscosity.

The fibers described herein have sufficient cohesive strength and integrity at their use temperature such that a web formed therefrom maintains its fibrous structure. Sufficient cohesiveness and integrity typically depends on the overall molecular weight of the polydiorganosiloxane polymer, and the concentration and nature of the amide linkages. Fibers comprising suitable polydiorganosiloxane polyamide (e.g. pressure sensitive adhesive) compositions typically exhibit relatively low or no cold flow, and display good aging properties, such that the fibers maintain their shape and desired properties (e.g., adhesive properties) over an extended period of time under ambient conditions.

In one favored embodiments, the fibers generally comprise a (e.g. linear) polydiorganosiloxane polyoxamide block copolymer. The block polydiorganosiloxane polyoxamide copolymer contains at least two repeat units of Formula I.

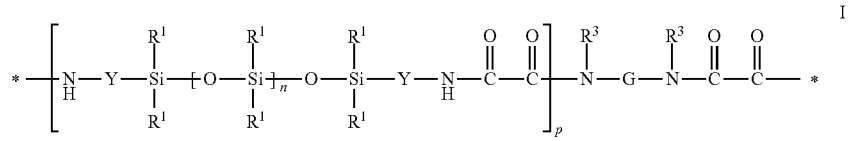

In this formula, each $R^1$ is independently an alkyl, haloalkyl, aralkyl, alkenyl, aryl, or aryl substituted with an alkyl, alkoxy, or halo, wherein at least 50 percent of the $R^1$ groups are methyl. Each Y is independently an alkylene, aralkylene, or a combination thereof. Subscript n is independently an integer of 40 to 1500 and the subscript p is an integer of 1 to 10. Group G is a divalent group that is the residue unit that is equal to a diamine of formula $R^3HN$-G-$NHR^3$ minus the two —$NHR^3$ groups. Group $R^3$ is hydrogen or alkyl (e.g., an alkyl having 1 to 10, 1 to 6, or 1 to 4 carbon atoms) or $R^3$ taken together with G and with the nitrogen to which they are both attached forms a heterocyclic group (e.g., $R^3HN$-G-$NHR^3$ is piperazine or the like). Each asterisk (*) indicates a site of attachment of the repeat unit to another group in the copolymer such as, for example, another repeat unit of Formula I.

Suitable alkyl groups for $R^1$ in Formula I typically have 1 to 10, 1 to 6, or 1 to 4 carbon atoms. Exemplary alkyl groups include, but are not limited to, methyl, ethyl, isopropyl, n-propyl, n-butyl, and iso-butyl. Suitable haloalkyl groups for $R^1$ often have only a portion of the hydrogen atoms of the corresponding alkyl group replaced with a halogen. Exemplary haloalkyl groups include chloroalkyl and fluoroalkyl groups with 1 to 3 halo atoms and 3 to 10 carbon atoms. Suitable alkenyl groups for $R^1$ often have 2 to 10 carbon atoms. Exemplary alkenyl groups often have 2 to 8, 2 to 6, or 2 to 4 carbon atoms such as ethenyl, n-propenyl, and n-butenyl. Suitable aryl groups for $R^1$ often have 6 to 12 carbon atoms. Phenyl is an exemplary aryl group. The aryl group can be unsubstituted or substituted with an alkyl (e.g., an alkyl having 1 to 10 carbon atoms, 1 to 6 carbon atoms, or 1 to 4 carbon atoms), an alkoxy (e.g., an alkoxy having 1 to 10 carbon atoms, 1 to 6 carbon atoms, or 1 to 4 carbon atoms), or halo (e.g., chloro, bromo, or fluoro). Suitable aralkyl groups for $R^1$ usually have an alkylene group having 1 to 10 carbon atoms and an aryl group having 6 to 12 carbon atoms. In some exemplary aralkyl groups, the aryl group is phenyl and the alkylene group has 1 to 10 carbon atoms, 1 to 6 carbon atoms, or 1 to 4 carbon atoms (i.e., the structure of the aralkyl is alkylene-phenyl where an alkylene is bonded to a phenyl group).

Preferably at least 50 percent of the $R^1$ groups are methyl. For example, at least 60 percent, at least 70 percent, at least 80 percent, at least 90 percent, at least 95 percent, at least 98 percent, or at least 99 percent of the $R^1$ groups can be methyl. The remaining $R^1$ groups can be selected from an alkyl having at least two carbon atoms, haloalkyl, aralkyl, alkenyl, aryl, or aryl substituted with an alkyl, alkoxy, or halo.

Each Y in Formula I is independently an alkylene, aralkylene, or a combination thereof. Suitable alkylene groups typically have up to 10 carbon atoms, up to 8 carbon atoms, up to 6 carbon atoms, or up to 4 carbon atoms. Exemplary alkylene groups include methylene, ethylene, propylene, butylene, and the like. Suitable aralkylene groups usually have an arylene group having 6 to 12 carbon atoms bonded to an alkylene group having 1 to 10 carbon atoms. In some exemplary aralkylene groups, the arylene portion is phenylene. That is, the divalent aralkylene group is phenylene-alkylene where the phenylene is bonded to an alkylene having 1 to 10, 1 to 8, 1 to 6, or 1 to 4 carbon atoms. As used herein with reference to group Y, "a combination thereof" refers to a combination of two or more groups selected from an alkylene and aralkylene group. A combination can be, for example, a single aralkylene bonded to a single alkylene (e.g., alkylene-arylene-alkylene). In one exemplary alkylene-arylene-alkylene combination, the arylene is phenylene and each alkylene has 1 to 10, 1 to 6, or 1 to 4 carbon atoms.

Each subscript n in Formula I is independently an integer of 40 to 1500. For example, subscript n can be an integer up to 1000, up to 500, up to 400, up to 300, up to 200, up to 100, up to 80, or up to 60. The value of n is often at least 40, at least 45, at least 50, or at least 55. For example, subscript n can be in the range of 40 to 1000, 40 to 500, 50 to 500, 50 to 400, 50 to 300, 50 to 200, 50 to 100, 50 to 80, or 50 to 60.

The subscript p is an integer of 1 to 10. For example, the value of p is often an integer up to 9, up to 8, up to 7, up to 6, up to 5, up to 4, up to 3, or up to 2. The value of p can be in the range of 1 to 8, 1 to 6, or 1 to 4.

Group G in Formula I is a residual unit that is equal to a diamine compound of formula $R^3HN$-G-$NHR^3$ minus the two amino groups (i.e., —$NHR^3$ groups). Group $R^3$ is hydrogen or alkyl (e.g., an alkyl having 1 to 10, 1 to 6, or 1 to 4 carbon atoms) or $R^3$ taken together with G and with the nitrogen to which they are both attached may form a heterocyclic group (e.g., $R^3HN$-G-$NHR^3$ is piperazine). The diamine can have primary or secondary amino groups. In most embodiments, $R^3$ is hydrogen or an alkyl. In many embodiments, both of the amino groups of the diamine are primary amino groups (i.e., both $R^3$ groups are hydrogen) and the diamine is of formula $H_2N$-G-$NH_2$.

In some embodiments, G is an alkylene, heteroalkylene, polydiorganosiloxane, arylene, aralkylene, or a combination thereof. Suitable alkylenes often have 2 to 10, 2 to 6, or 2 to 4 carbon atoms. Exemplary alkylene groups include ethylene, propylene, butylene, and the like. Suitable heteroalkylenes are often polyoxyalkylenes such as polyoxyethylene having at least 2 ethylene units, polyoxypropylene having at least 2 propylene units, polyoxybutylene or copolymers thereof. Suitable polydiorganosiloxanes include the polydiorganosiloxane diamines of Formula III, which are described below, minus the two amino groups. Exemplary polydiorganosiloxanes include, but are not limited to, polydimethylsiloxanes with alkylene Y groups. Suitable aralkylene groups usually contain an arylene group having 6 to 12 carbon atoms bonded to an alkylene group having 1 to 10 carbon atoms. Some exemplary aralkylene groups are phenylene-alkylene where the phenylene is bonded to an alkylene having 1 to 10 carbon atoms, 1 to 8 carbon atoms, 1 to 6 carbon atoms, or 1 to 4 carbon atoms. As used herein with reference to group G, "a combination thereof" refers to a combination of two or more groups selected from an alkylene, heteroalkylene, polydiorganosiloxane, arylene, and aralkylene. A combination can be, for example, an aralkylene bonded to an alkylene (e.g., alkylene-arylene-alkylene).

In one exemplary alkylene-arylene-alkylene combination, the arylene is phenylene and each alkylene has 1 to 10, 1 to 6, or 1 to 4 carbon atoms.

The polydiorganosiloxane polyoxamide tends to be free of groups having a formula —$R^a$—(CO)—NH— where $R^a$ is an alkylene. All of the carbonylamino groups along the backbone of the copolymeric material are part of an oxalylamino group (i.e., the —(CO)—(CO)—NH— group). That is, any carbonyl group along the backbone of the copolymeric material is bonded to another carbonyl group and is part of an oxalyl group. More specifically, the polydiorganosiloxane polyoxamide has a plurality of aminoxalylamino groups.

The polydiorganosiloxane polyoxamide is a linear, block copolymer and can be an elastomeric material. Unlike many of the known polydiorganosiloxane polyamides that are generally formulated as brittle solids or hard plastics, the polydiorganosiloxane polyoxamides can be formulated to include greater than 50 weight percent polydiorganosiloxane segments based on the weight of the copolymer. The weight percent of the diorganosiloxane in the polydiorganosiloxane polyoxamides can be increased by using higher molecular weight polydiorganosiloxanes segments to provide greater than 60 weight percent, greater than 70 weight percent, greater than 80 weight percent, greater than 90 weight percent, greater than 95 weight percent, or greater than 98 weight percent of the polydiorganosiloxane segments in the polydiorganosiloxane polyoxamides. Higher amounts of the polydiorganosiloxane can be used to prepare elastomeric materials with lower modulus while maintaining reasonable strength.

The polydiorganosiloxane polyoxamide copolymers have many of the desirable features of polysiloxanes such as low glass transition temperatures, thermal and oxidative stability, resistance to ultraviolet radiation, low surface energy and hydrophobicity, and high permeability to many gases. Additionally, the copolymers exhibit good to excellent mechanical strength.

The copolymeric material of Formula I can be optically clear. As used herein, the term "optically clear" refers to a material that is clear to the human eye. An optically clear copolymeric material often has a luminous transmission of at least about 90 percent, a haze of less than about 2 percent, and opacity of less than about 1 percent in the 400 to 700 nm wavelength range. Both the luminous transmission and the haze can be determined using, for example, the method of ASTM-D 1003-95.

The linear block copolymers having repeat units of Formula I can be prepared, for example by reaction of at least one polydiorganosiloxane-containing precursor with at least one diamine as described in U.S. Pat. No. 7,371,464; incorporated herein by reference.

The diamines are sometimes classified as organic diamines or polydiorganosiloxane diamines with the organic diamines including, for example, those selected from alkylene diamines, heteroalkylene diamines (such as polyoxyalkylene diamines), arylene diamines, aralkylene diamines, or alkylene-aralkylene diamines. The diamine has only two amino groups so that the resulting polydiorganosiloxane polyoxamides are linear block copolymers that are often elastomeric, hot melt processable (e.g., the copolymers can be processed at elevated temperatures such as up to 250° C. or higher without apparent degradation of the composition), and soluble in some common organic solvents. The some embodiments, the diamine is free of a polyamine having more than two primary or secondary amino groups. Tertiary amines that do not react with the polydiorganosiloxane-containing precursor of can also be present. Additionally, the diamines utilized in the reaction are free of any carbonylamino group. That is, the diamine is not an amide.

Preferred alkylene diamines (i.e., G is a alkylene) include, but are not limited to, ethylene diamine, propylene diamine, butylene diamine, hexamethylene diamine, 2-methylpentamethylene 1,5-diamine (i.e., commercially available from DuPont, Wilmington, Del. under the trade designation DYTEK A), 1,3-pentane diamine (commercially available from DuPont under the trade designation DYTEK EP), 1,4-cyclohexane diamine, 1,2-cyclohexane diamine (commercially available from DuPont under the trade designation DHC-99), 4,4'-bis(aminocyclohexyl)methane, and 3-aminomethyl-3,5,5-trimethylcyclohexylamine.

The polydiorganosiloxane polyoxamide copolymer can be produced using a plurality of polydiorganosiloxane precursors, a plurality of diamines, or a combination thereof. A plurality of precursors having different average molecular weights can be combined under reaction conditions with a single diamine or with multiple diamines. For example, the precursor of may include a mixture of materials with different values of n, different values of p, or different values of both n and p. The multiple diamines can include, for example, a first diamine that is an organic diamine and a second diamine that is a polydiorganosiloxane diamine. Likewise, a single precursor can be combined under reaction conditions with multiple diamines.

Any suitable reactor or process can be used to prepare the polydiorganosiloxane polyamide copolymer material. The reaction can be conducted using a batch process, semi-batch process, or a continuous process. Exemplary batch processes can be conducted in a reaction vessel equipped with a mechanical stirrer such as a Brabender mixer, provided the product of the reaction is in a molten state has a sufficiently low viscosity to be drained from the reactor. Exemplary semi-batch process can be conducted in a continuously stirred tube, tank, or fluidized bed. Exemplary continuous processes can be conducted in a single screw or twin screw extruder such as a wiped surface counter-rotating or co-rotating twin screw extruder.

The polydiorganosiloxane-containing precursor can be prepared by any known method. In some embodiments, this precursor is prepared according to the following reaction scheme, as described in previously cited U.S. Pat. No. 7,371,464.

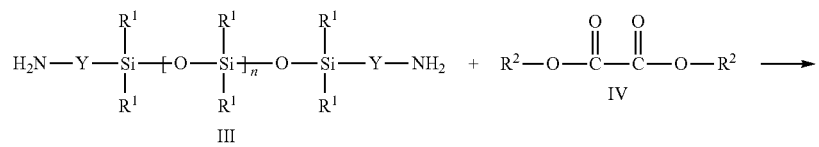

-continued

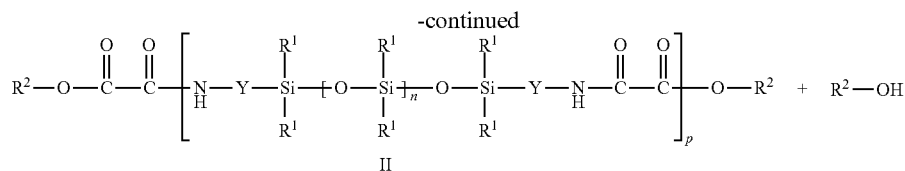

II

The polydiorganosiloxane diamine can be prepared by any known method and can have any suitable molecular weight. In favored embodiments, the average molecular weight is at least 10,000 g/mole and typically no greater than 150,000 g/mole.

Suitable polydiorganosiloxane diamines and methods of making the polydiorganosiloxane diamines are described, for example, in U.S. Pat. No. 5,214,119 (Leir et al.), U.S. Pat. No. 5,461,134 (Leir et al.), U.S. Pat. No. 5,512,650 (Leir et al.), and U.S. Pat. No. 7,371,464 (Sherman et al.), incorporated herein by reference in their entirety. Some polydiorganosiloxane diamines are commercially available, for example, from Shin Etsu Silicones of America, Inc., Torrance, Calif. and from Gelest Inc., Morrisville, Pa.

Tackifying resins such as silicate tackifying resins are added to the polydiorganosiloxane polyoxamide copolymer to provide or enhance the adhesive properties of the copolymer. The silicate tackifying resin can influence the physical properties of the resulting adhesive composition. For example, as silicate tackifying resin content is increased, the glassy to rubbery transition of the adhesive composition occurs at increasingly higher temperatures. In some exemplary adhesive compositions, a plurality of silicate tackifying resins can be used to achieve desired performance.

Suitable silicate tackifying resins include those resins composed of the following structural units M (i.e., monovalent $R'_3SiO_{1/2}$ units), D (i.e., divalent $R'_2SiO_{2/2}$ units), T (i.e., trivalent $R'SiO_{3/2}$ units), and Q (i.e., quaternary $SiO_{4/2}$ units), and combinations thereof. Typical exemplary silicate resins include MQ silicate tackifying resins, MQD silicate tackifying resins, and MQT silicate tackifying resins. These silicate tackifying resins usually have a number average molecular weight in the range of 100 to 50,000 or in the range of 500 to 15,000 and generally have methyl R' groups.

MQ silicate tackifying resins are copolymeric resins having $R'_3SiO_{1/2}$ units ("M" units) and $SiO_{4/2}$ units ("Q" units), where the M units are bonded to the Q units, each of which is bonded to at least one other Q unit. Some of the $SiO_{4/2}$ units ("Q" units) are bonded to hydroxyl radicals resulting in $HOSiO_{3/2}$ units ("$T^{OH}$" units), thereby accounting for the silicon-bonded hydroxyl content of the silicate tackifying resin, and some are bonded only to other $SiO_{4/2}$ units.

Such resins are described in, for example, *Encyclopedia of Polymer Science and Engineering*, vol. 15, John Wiley & Sons, New York, (1989), pp. 265-270, and U.S. Pat. No. 2,676,182 (Daudt et al.), U.S. Pat. No. 3,627,851 (Brady), U.S. Pat. No. 3,772,247 (Flannigan), and U.S. Pat. No. 5,248,739 (Schmidt et al.). Other examples are disclosed in U.S. Pat. No. 5,082,706 (Tangney). The above-described resins are generally prepared in solvent. Dried or solventless, M silicone tackifying resins can be prepared, as described in U.S. Pat. No. 5,319,040 (Wengrovius et al.), U.S. Pat. No. 5,302,685 (Tsumura et al.), and U.S. Pat. No. 4,935,484 (Wolfgruber et al.).

Certain MQ silicate tackifying resins can be prepared by the silica hydrosol capping process described in U.S. Pat. No. 2,676,182 (Daudt et al.) as modified according to U.S. Pat. No. 3,627,851 (Brady), and U.S. Pat. No. 3,772,247 (Flannigan). These modified processes often include limiting the concentration of the sodium silicate solution, and/or the silicon-to-sodium ratio in the sodium silicate, and/or the time before capping the neutralized sodium silicate solution to generally lower values than those disclosed by Daudt et al. The neutralized silica hydrosol is often stabilized with an alcohol, such as 2-propanol, and capped with $R_3SiO_{1/2}$ siloxane units as soon as possible after being neutralized. The level of silicon bonded hydroxyl groups (i.e., silanol) on the MQ resin may be reduced to no greater than 1.5 weight percent, no greater than 1.2 weight percent, no greater than 1.0 weight percent, or no greater than 0.8 weight percent based on the weight of the silicate tackifying resin. This may be accomplished, for example, by reacting hexamethyldisilazane with the silicate tackifying resin. Such a reaction may be catalyzed, for example, with trifluoroacetic acid. Alternatively, trimethylchlorosilane or trimethylsilylacetamide may be reacted with the silicate tackifying resin, a catalyst not being necessary in this case.

MQD silicone tackifying resins are terpolymers having $R'_3SiO_{1/2}$ units ("M" units), $SiO_{4/2}$ units ("Q" units), and $R'_2SiO_{2/2}$ units ("D" units) such as are taught in U.S. Pat. No. 2,736,721 (Dexter). In MQD silicone tackifying resins, some of the methyl R' groups of the $R'_2SiO_{2/2}$ units ("D" units) can be replaced with vinyl ($CH_2=CH-$) groups ("$D^{Vi}$" units).

MQT silicate tackifying resins are terpolymers having $R'_3SiO_{1/2}$ units, $SiO_{4/2}$ units and $R'SiO_{3/2}$ units ("T" units) such as are taught in U.S. Pat. No. 5,110,890 (Butler) and Japanese Kokai HE 2-36234.

Suitable silicate tackifying resins are commercially available from sources such as Dow Corning, Midland, Mich., General Electric Silicones Waterford, N.Y. and Rhodia Silicones, Rock Hill, S.C. Examples of particularly useful MQ silicate tackifying resins include those available under the trade designations SR-545 and SR-1000, both of which are commercially available from GE Silicones, Waterford, N.Y. Such resins are generally supplied in organic solvent and may be employed in the formulations of the adhesives of as received. Blends of two or more silicate resins can be included in the adhesive compositions.

The pressure sensitive adhesive compositions typically contain at least 20 to 80 weight percent polydiorganosiloxane polyamide and 20 to 80 weight percent silicate tackifying resin based on the combined weight of polydiorganosiloxane polyamide and silicate tackifying resin. For example, the adhesive compositions can contain 30 to 70 weight percent polydiorganosiloxane polyamide and 30 to 70 weight percent silicate tackifying resin, 35 to 65 weight percent polydiorganosiloxane polyamide and 35 to 65 weight percent silicate tackifying resin, 40 to 60 weight percent polydiorganosiloxane polyamide and 40 to 60 weight percent silicate tackifying resin, or 45 to 55 weight percent polydiorganosiloxane polyamide and 45 to 55 weight percent silicate tackifying resin.

In some embodiments, multi-component fibers are described. The multi-component fibers comprise at least one polydiorganosiloxane polyamide and at least one second polymer (inclusive of copolymers) that is not a polydiorganosiloxane polymer. These different components can be in the form of two or more layered fibers, sheath-core fiber arrangements, fibers with multiple radial segments (e.g. wherein a cross-section of the fiber has a pie arrangement of alternating polydiorganosiloxane polyamide and second melt processable polymer) or in "island in the sea" type fiber structures. At least one layer (e.g. core and/or outer layer) of the multilayered fibers, is present substantially continuously along the fiber length in discrete zones, which zones preferably extend along the entire length of the fibers. In some embodiments, the outer layer is discontinuous along the fiber length.

Regardless of the physical form of the multi-component fiber, in favored embodiments a substantial portion of the outer surface of the fiber comprises a polydiorganosiloxane polyamide polymer or pressure sensitive adhesive composition comprising such. In some embodiments, the polydiorganosiloxane polyamide composition comprises at least 25%, 30%, 35%, 40%, 45% or 50% of the outer surface layer of the fibers. In a classic sheath-core fiber arrangement, the entire outer layer may consist of the polydiorganosiloxane polyamide (e.g. adhesive) composition. Typically, however, a portion of the outer layer comprises the second thermoplastic polymer. Thus, in this embodiment, the polydiorganosiloxane polyamide (e.g. adhesive) comprises less than 100% of the outer surface layer. In some embodiments, the polydiorganosiloxane polyamide (e.g. adhesive) comprises at least 55%, 60%, 65%, 70%, 75%, 80%, 85%, 90%, or 95% of the outer surface layer of the fibers.

The second polymer(s) are melt processable (typically, thermoplastic) and may or may not have elastomeric properties. They also may or may not have pressure sensitive adhesive properties. Such polymers (referred to herein as second melt processable polymers or copolymers) have relatively low shear viscosity in the melt such that they can be readily extruded, and drawn effectively to form fibers, as described above with respect to the polydiorganosiloxane polyamide composition. Although the second polymer may be miscible with the polydiorganosiloxane polyamide composition, the materials are generally processed such that the outer surface layer is predominantly the polydiorganosiloxane polyamide (e.g. adhesive) composition. The rheological behavior in the melt of the polymers is typically similar in order to facilitate a uniform extrusion.

The second melt processable polymer can provide various improvements. In some embodiments, the second melt processable polymer reduces the cost of the overall web. In other embodiments, the second melt processable polymer can increase the elasticity of the core layer, which can improve adhesion (e.g. to skin). In yet other embodiments, the second melt processable polymer can adjust the adhesion level. For example, by use of a second melt processable polymer that is a (e.g. acrylic copolymer) pressure sensitive adhesive, the peel strength can be increased. However, by use of other second melt processable polymers, such as polyolefins, the peel strength can be decreased. In yet other embodiments, the second melt processable polymer can improve adhesion or anchoring to another substrate, such as a backing. For example, the inclusion of a polyolefin second melt processable polymer wherein at least a portion is present on the external layer can improve adhesion to polyolefin backing materials.

The second melt processable polymers or copolymers can be used in various amounts. In favored embodiments, the concentration of a lower cost second melt processable polymers is maximized, while still providing the benefits of the inclusion of the polydiorganosiloxane polyamide (e.g. pressure sensitive adhesive) composition. The second melt processable polymer(s) or copolymer(s) is typically present in an amount of at least 25 wt-%, 30 wt-%, 35 wt-%, 40 wt-%, 45 wt-%, 50 wt-%, 55 wt-%, 60 wt-%, 65 wt-% or about 70 wt-%, based on the total weight of the multicomponent fiber or nonwoven web.

Examples of second melt processable polymers or copolymers include, but are not limited to, polyolefins such as polyethylene, polypropylene, polybutylene, polyhexene, and polyoctene; polystyrenes; polyurethanes; polyesters such as polyethyleneterephthalate; polyamides such as nylon; styrenic block copolymers of the type available under the trade designation KRATON (e.g., styrene/isoprene/styrene, styrene/butadiene/styrene); epoxies; -acrylic polymer and copolymers (i.e. polyacrylates); vinyl acetates such as ethylene vinyl acetate; and mixtures thereof.

In some embodiments, the second melt processable polymer is a pressure sensitive adhesive composition. For example, the second melt processable polymer may be an acrylate pressure sensitive adhesive, as described in U.S. Pat. No. 6,083,856, incorporated herein by reference; or a tackified styrenic block copolymer pressure sensitive adhesive composition.

Polyacrylate pressure sensitive adhesives are often derived from: (A) at least one monofunctional alkyl (meth) acrylate monomer (i.e., alkyl acrylate and alkyl methacrylate monomer); and (B) at least one monofunctional free-radically copolymerizable reinforcing monomer. The reinforcing monomer has a homopolymer glass transition temperature higher than that of the alkyl (meth)acrylate monomer. Preferably, the monomers used in preparing the polyacrylate pressure-sensitive adhesive copolymer fibers include: (A) a monofunctional alkyl (meth)acrylate monomer that, when homopolymerized, generally has a glass transition temperature of no greater than about 0° C.; and (B) a monofunctional free-radically copolymerizable reinforcing monomer that, when homopolymerized, generally has a glass transition temperature of at least about 10° C., as measured by differential scanning calorimetry. The alkyl group of the (meth)acrylate typically has an average of about 4 to about 20 carbon atoms, and more preferably, an average of about 4 to about 14 carbon atoms. The alkyl group can optionally contain oxygen atoms in the chain thereby forming ethers or alkoxy ethers. Reinforcing monomer B is typically (meth) acrylic monomer, including an acrylic acid, a methacrylic acid, an acrylamide, and an acrylate. The polyacrylate pressure sensitive adhesive may be prepared by reacting acrylate macromers of polystyrene, methocy terminated polyethylene glycol, and the like. In one embodiments, the polyacrylate pressure sensitive adhesive is prepared by grafting a polystyrene macromer onto a random copolymer of A and B.

For embodiments wherein the multi-component fiber comprises a second melt processable polymer or copolymer that lacks a tackifying resin, the total amount of tackifying resin in the pressure sensitive melt blown web can be less than that of the adhesive alone. For example, when the pressure sensitive polydiorganosiloxane polyamide outer layer typically comprises 40 to 60 weight percent silicate tackifying resin, the concentration of silicate tackifying resin in the melt blown web can be at least 15 wt-% or 20 wt-%. Alternatively, when the second melt processable polymer or copolymer comprises a tackifying resin, the fiber may have a greater concentration of tackifying resin than the polydiorganosiloxane polyamide pressure sensitive adhesive.

The polydiorganosiloxane polyamide (e.g. adhesive) composition and the second melt processable polymer can further include other additives to provide desired properties. For example, dyes and pigments can be added as colorant; electrically and/or thermally conductive compounds can be added to make the composition electrically and/or thermally conductive or antistatic; antioxidants and antimicrobial agents can be added; and ultraviolet light stabilizers and absorbers, such as hindered amine light stabilizers (HALS), can be added to stabilize the composition against ultraviolet degradation and to block certain ultraviolet wavelengths from passing through the article. Other additives include, but are not limited to, adhesion promoters, fillers, tack enhancers (i.e. tackifiers), blowing agents, melt processable diluents such as plasticizers, and flame-retardants.

Melt processes for the preparation of fibers such as spunbond and melt-blown processes are well-known in the art. Although the multi-component fiber can be prepared from any suitable process, the composition is preferably prepared into fibers, particularly microfibers, and nonwoven webs thereof, with a melt-blown process as described in U.S. Pat. Nos. 5,238,733 and 6,083,856 (Joseph et al.); incorporated herein by reference.

Melt-blown processes are particularly preferred because they form autogenously bonded webs that typically require no further processing to bond the fibers together. The melt-blown processes used in the formation of multilayer microfibers as disclosed in the Joseph et al. patents listed above are particularly suitable for use in making the multi-layer microfibers described herein. Such processes use hot (e.g., equal to or about 20° C. to about 30° C. higher than the polymer melt temperature), high-velocity air to draw out and attenuate extruded polymeric material from a die, which will generally solidify after traveling a relatively short distance from the die. Depending on the processing temeprature and conditions, the melt-blown fibers thus formed can be unoriented (i.e. lack orientation). The resultant fibers are termed melt-blown fibers and are generally substantially continuous. They form into a coherent web between the exit die orifice and a collecting surface by entanglement of the fibers due in part to the turbulent airstream in which the fibers are entrained.

For example, the Joseph et al. patents describe forming a multi-component melt-blown microfiber web by feeding two separate flow streams of organic polymeric material into a separate splitter or combining manifold. The split or separated flow streams are generally combined immediately prior to the die or die orifice. The separate flow streams are preferably established into melt streams along closely parallel flow paths and combined where they are substantially parallel to each other and the flow path of the resultant combined multilayered flow stream. This multilayered flow stream is then fed into the die and/or die orifices and through the die orifices. Air slots are disposed on either side of a row of the die orifices directing uniform heated air at high velocities at the extruded multi-component melt streams. The hot high velocity air draws and attenuates the extruded polymeric material which solidified after traveling a relatively short distance from the die. Single layer microfibers can be made in an analogous manner with air attenuation using a single extruder, no splitter, and a single port feed die.

The temperature and selection of melt processable material of the separate flowstreams is typically controlled to bring the (e.g. pressure sensitive adhesive) polydiorganosiloxane polyamide and second melt processable polymers to sufficiently similar viscosities, as previously described. When the separate polymer flowstreams converge, the flowstreams generally have an apparent viscosity in the melt (i.e., at melt blowing conditions) of about 150 poise to about 800 poise, as determined using a capillary rheometer. The apparent viscosities of the polymeric flowstream(s) can be adjusted by varying the temperatures as per U.S. Pat. No. 3,849,241 (Butin, et al).

In some embodiments, the second melt processable polymer has the same or similar complex viscosity characteristics as previously described for the low surface energy thermoplastic composition. Typically, however, the second melt processable polymer will be melt blown at a lower temperature than the polydiorganosiloxane polyamide (e.g. pressure sensitive adhesive). In some embodiments, the second melt processable polymer is melt blown at a temperature at least 10° C., or 20° C., or 30° C., or 40° C. lower than the polydiorganosiloxane polyamide composition. Hence, at the same temperature the second melt processable polymer typically has a substantially lower viscosity.

The ratio of complex viscosity at the melt blowing temperature between the polydiorganosiloxane polyamide (e.g. pressure sensitive adhesive) composition and second melt processable polymer typically varies from about 1:1 to about 10:1 (i.e. the polydiorganosiloxane polyamide (e.g. adhesive) composition being 10× more viscous than the second melt processable polymer). In some embodiments, the ratio of complex viscosity at the melt blowing temperature between the polydiorganosiloxane polyamide composition and second melt processable polymer is no greater than 9:1, or 8:1, or 7:1, or 6:1, or 5:1.

The solidified or partially solidified fibers form an interlocking network of entangled fibers, that are collected as a web. The collecting surface can be a solid or perforated surface in the form of a flat surface or a drum, a moving belt, or the like. If a perforated surface is used, the backside of the collecting surface can be exposed to a vacuum or low-pressure region to assist in the deposition of the fibers. The collector distance is generally about 7 centimeters (cm) to about 130 cm from the die face. Moving the collector closer to the die face, e.g., about 7 cm to about 30 cm, will result in stronger inter-fiber bonding and a less lofty web.

The size of the polymeric fibers formed depends to a large extent on the velocity and temperature of the attenuating airstream, the orifice diameter, the temperature of the melt stream, and the overall flow rate per orifice. The webs formed can be of any suitable thickness for the desired and intended end use. Generally, a thickness of about 0.01 cm to about 1 or 0.5 cm is suitable for most applications. Typically, the thickness will be 0.025 to 0.25 cm. The basis weight of the nonwoven web typically ranges from about 5 grams/m$^2$ to about 100, 125, or 150 grams/m$^2$ microns. In some embodiments, the basis weight is at least 10, 15 or 20 grams/m$^2$. In other embodiments, the basis weight may be at least 50, 60 or 70 grams/m$^2$ The polydiorganosiloxane polyamide pressure sensitive and multi-component fibers described herein can be mixed with other fibers, such as staple fibers. Webs having more than one type of fiber are referred to herein as having commingled constructions. In commingled constructions, the various types of fibers can be intimately mixed forming a substantially uniform cross-section, or they can be in separate layers. The web properties can be varied by the number of different fibers used, the number of layers employed, and the layer arrangement. Other materials, such as surfactants or binders can also be incorporated into the web before, during, or after its collection, such as by the use of a spray jet.

Webs or composite structures including the webs can be further processed after collection or assembly, such as by calendaring or point embossing to increase web strength, provide a patterned surface, or fuse fibers at contact points in a web structure or the like; by orientation to provide increased web strength; by needle punching; heat or molding operations; coating, such as with adhesives to provide a tape structure; or the like.

The nonwoven webs described herein can be used in composite multi-layer structures. The other layers can be supporting webs, nonwoven webs of spun bond, staple, and/or melt-blown fibers, as well as films of elastic, semipermeable, and/or impermeable materials. These other layers can be used for absorbency, surface texture, rigidification, etc. They can be attached to the nonwoven webs of the fibers using conventional techniques such as heat bonding, binders or adhesives, or mechanical engagement such as hydroentanglement or needle punching.

The nonwoven webs described herein can be used to prepare a laminate comprising a backing and a pressure sensitive adhesive nonwoven web as described herein. That is, those nonwoven webs can be used as a pressure sensitive adhesive layer on a backing, such as paper, a polymeric film, or a conventional woven or nonwoven web, to form an adhesive article. The pressure sensitive adhesive nonwoven web may be covered by a release liner until use. The nonwoven webs described herein can be also be used to bond other layers together, especially other nonwoven layers.

The nonwoven webs described herein can be used to prepare adhesive articles, such as tapes, including medical grade tapes that adhere to skin, labels, wound dressings, so-called incise drapes that are adhered to the skin of a patient prior to making a surgical incision directly through the drape and the like.

Suitable backing materials, especially for medical drapes and dressings, include elastomeric films including polyolefins, such as low density polyethylene and particularly metallocene polyethylenes such as Engage™ polyethylenes commercially available from Dow Chemical, polyurethanes such as polyester or polyether polyurethanes (e.g., "Estane™ thermoplastic polyurethane," commercially available from Lubrizol Corp., Wickliffe, Ohio), polyesters such as polyether polyester (e.g., "Hytrel™ polyester elastomer," commercially available from Du Pont Co., Wilmington, Del.), and polyamides such as polyether polyamides (e.g., "Pebax™ Resins" commercially available from ELF Atochem, North America, Inc., Philadelphia, Pa.).

Preferred films and PSA coated dressings and drapes have a high moisture vapor transmission rate (MVTR), as measured according to the test method described in the examples. The MVTR is typically greater than 1000 g/m$^2$/24 hrs, or 2000 g/m$^2$/24 hrs, or 3000 g/m$^2$/24 hrs (at 37° C./100-20% relative humidity). In some embodiments, the MVTR is greater than 4000 g/m$^2$/24 hrs, or 5000 g/m$^2$/24 hrs, or 6000 g/m$^2$/24 hrs, or 7000 g/m$^2$/24 hrs, or 8000 g/m$^2$/24 hrs.

The polysiloxane polyamide PSAs fibers or non-wovens may be suitable for use with microreplicated fluid transport dressings such as those disclosed in U.S. Pat. No. 7,781,639; which is incorporated herein by reference.

In some preferred embodiments the polydiorganosiloxane polyamide copolymer may have incorporated therein or thereon one or more suitable antimicrobial agents. The use of an antimicrobial agent can be particularly useful for topical applications such as wound dressings, incise drapes, IV dressings, first aid dressings, medical tapes, wound contact layers, and the like. The antimicrobial agent includes an antimicrobial lipid, a phenolic antiseptic, a cationic antiseptic, iodine and/or an iodophor, an antimicrobial natural oil, or combinations thereof. In addition to or in place of the antimicrobial in or on the fiber comprising the polydiorganosiloxane polyamide PSA, the medical article may have antimicrobial delivered from one or more other components such as a nonwoven or foam layer, the backing, a thin film contact layer and the like.

In certain embodiments, the antimicrobial lipid is selected from the group consisting of a (C7-C14) saturated fatty acid ester of a polyhydric alcohol, a (C8-C22) unsaturated fatty acid ester of a polyhydric alcohol, a (C7-C14) saturated fatty ether of a polyhydric alcohol, a (C8-C22) unsaturated fatty ether of a polyhydric alcohol, a (C7-C14) fatty alcohol ester (preferably a monoester) of a (C2-C8)hydroxycarboxylic acid (preferably a (C8-C12) fatty alcohol ester (preferably a monoester) of a (C2-C8)hydroxycarboxylic acid), a (C8-C22) mono- or poly-unsaturated fatty alcohol ester (preferably a monoester) of a (C2-C8)hydroxycarboxylic acid, an alkoxylated derivative of any of the foregoing having a free hydroxyl group, and combinations thereof; wherein the alkoxylated derivative has less than 5 moles of alkoxide per mole of polyhydric alcohol or hydroxycarboxylic acid; with the proviso that for polyhydric alcohols other than sucrose, the esters comprise monoesters and the ethers comprise monoethers, and for sucrose the esters comprise monoesters, diesters, or combinations thereof, and the ethers comprise monoethers.

In certain embodiments, the antimicrobial lipid is selected from the group consisting of a (C8-C12) saturated fatty acid ester of a polyhydric alcohol, a (C12-C22) unsaturated fatty acid ester of a polyhydric alcohol, a (C8-C12) saturated fatty ether of a polyhydric alcohol, a (C12-C22) unsaturated fatty ether of a polyhydric alcohol), an alkoxylated derivative of any of the foregoing, and combinations thereof; wherein the alkoxylated derivative has less than 5 moles of alkoxide per mole of polyhydric alcohol; with the proviso that for polyhydric alcohols other than sucrose, the esters comprise monoesters and the ethers comprise monoethers, and for sucrose the esters comprise monoesters, diesters, or combinations thereof, and the ethers comprise monoethers.

In certain embodiments, the antimicrobial component includes a phenolic antiseptic. In certain embodiments, the phenolic antiseptic is selected from the group consisting of diphenyl ethers, phenolics, bisphenolics, resorcinols, anilides, and combinations thereof. In certain embodiments, the phenolic antiseptic comprises triclosan.

In certain embodiments, the antimicrobial component includes a cationic antiseptic. In certain embodiments, the cationic antiseptic is selected from the group consisting of biguanides, bisbiguanides, polymeric biguanides, including but not limited to chlorhexidine salts and polyhexamethylene biguanide salts, polymeric quaternary ammonium compounds, silver and its complexes, small molecule quaternary ammonium compounds comprising a quaternary ammonium or protonated tertiary or secondary amine and at least one alkyl group of at least 6 carbon atoms such as benzethonium chloride, methylbenzethonium chloride, benzalkonium chloride, cetylpyridinium chloride, cetyltrimethylammonium bromide, octenidine, and the like, and combinations thereof.

In certain embodiments the cationic antimicrobial component includes silver and copper. Silver is also known to be an effective antiseptic and has been used in creams to treat wounds and other topical infections. The active form of silver is the ion Ag+ which may be delivered from a variety of well known silver salts and complexes including silver zeolites; inorganic silver salts such as silver nitrate, silver chloride, silver sulfate, silver thiosulfate; silver alkyl, aryl, and aralkyl carboxylates (preferred carboxylate anions have less than about 8 carbon atoms such as the acetate, lactate, salicylate, and gluconate salts); silver oxide, colloidal silver, nanocrystalline silver, silver zeolites, silver coated microspheres, silver complexed with various polymers as well as silver delivered from dendrimers as described in U.S. Pat. Nos. 6,579,906 and 6,224,898; and silver antimicrobial complexes such as silver sufadiazine. The silver may optionally complexed with primary, secondary, tertiary, and quaternary amines as well as polymeric forms thereofs, and silver protein complexes.

In certain embodiments, the antimicrobial component includes iodine and/or an iodophor. In certain embodiments, the iodophor is povidone-iodine or a polyethyleneglycol-iodine or derivatized polyethylene glycol-iodine complex such as a polyethyoxylated alkyl or alkaryl alcohol-iodine complex. As used herein an iodine complex may include complexes with molecular iodine but are more often complexes with triiodide.

In certain embodiments, the antimicrobial component includes an antimicrobial natural oil. The natural oil antiseptics includes oils and oil extracts from plants such as Tea Tree oil, grape fruit seed extract, Aspidium extract (phloro, lucinol containing extract); barberry extract (berberine chloride); bay sweet extract; bayberry bark extract (myricitrin); cade oil; CAE (available from Ajinomoto, located in Teaneck, N.J.); cajeput oil; caraway oil; cascarilla bark (sold under the tradename ESSENTIAL OIL); cedarleaf oil; chamomille; cinnamon oil; citronella oil; clove oil; German chamomile oil; giant knotweed; lemon balm oil; lemon grass; olive leaf extract (available from Bio Botanica); parsley; patchouly oil; peony root; pine needle oil; PLAN-SERVATIVE (available from Campo Research); rose geranium oil; rosemary; sage, and the like, as well as mixtures thereof. Particularly preferred are tea tree oil (cajeput oil) and grapefruit seed extract.

EXAMPLES

Materials Employed

A1: Hot Melt Acrylate Pressure Sensitive Adhesive (PSA)

Polymer A1 was a copolymer of isooctyl acrylate/acrylic acid/polystyrene macromer, having a composition of 92/4/4% (by weight), respectively. First, a random copolymer of isooctyl acrylate and acrylic acid was made, and this polymer was then grafted with a polystyrene macromer. The polymer was made as described in Example 1 of U.S. Pat. No. 6,083,856 and the reference cited therein.

Melt viscosity under oscillatory shear was measured with an ARES G2 rheometer (TA Instruments, New Castle, Del., USA) using parallel plate fixtures. A specimen of the polymer was molded into a disk of 25 mm diameter and 1 mm thickness, which was placed between the parallel plates. Using the temperature sweep method, viscosity was measured while the sample was heated at 1° C./min. Strain amplitude was set at 3% and frequency was set at 1 Hz. Complex viscosity was measured and reported in poise. The complex viscosity of acrylic adhesive A1 in the melt state at 200° C. was 600 poise.

P1: Polyolefin Blend

Polymer P1 was a blend of ENGAGE 8401 Polyolefin Elastomer, a copolymer of ethylene and octene-1 (The Dow Chemical Company, Midland, Mich. USA) and DOW DNDA-1081 NT 7 Linear Low Density Polyethylene (LL-DPE) (The Dow Chemical Company, Midland, Mich. USA). P1 was prepared by blending the pellets of ENGAGE 8401 and LLDPE at a composition of 80/20 (ENGAGE/LLDPE) by weight. Melt viscosity was measured by the same technique used for polymer A1. The complex viscosity of polyolefin blend P1 in the melt state at 200° C. was 3000 poise.

S1: Silicone Polyoxamide Pressure Sensitive Adhesive (PSA)

Polymer Compound S1 was a blend of a Silicone Polyoxamide elastomer and an MQ-RESIN The Silicone polyoxamide polymer used is indicated by this structural formula

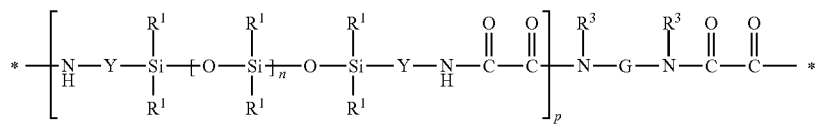

in which Y=propylene, R1=methyl, R3=H, and G=ethylene. It was prepared according to the method of Example 2 in U.S. Pat. No. 7,501,184, with the exception that instead of a 5,000 molecular weight polydimethylsiloxane diamine, a PDMS diamine having an approximate molecular weight of 25,000 g/mol was used. The 25,000 MW silicone diamine was prepared as described in U.S. Pat. No. 6,355,759.

To prepare the silicone polyoxamide, a molar ratio of amine (from ethylene diamine) to ester (from the precursor) of 0.92:1 was used.

Inherent Viscosity (IV) of this Silicone polyoxamide polymer was measured at 30° C., using a Canon-Fenske viscometer (Model No. 50 P296), in a tetrahydrofuran (THF) solution at a concentration of 0.2 g/dL. Inherent viscosities of similar Silicone polyoxamide polymers have been found previously to be essentially independent of concentration in the range of 0.1 to 0.4 g/dL. The inherent viscosity was averaged over 3 runs. The Silicone polyoxamide resin had an IV of 1.6 dl/g.

MQ-RESIN POWDER 803 TF (Wacker Chemie AG, München, Germany) was obtained commercially and is believed to be a co-hydrolysis product of tetraalkoxy silane (Q unit) and trimethyl-ethoxy silane (M unit). The chemical structure of MQ-RESIN POWDER 803 TF is believed to be a three dimensional network of polysilicic acid units which are endblocked with trimethylsilyl groups. Some residual ethoxy and hydroxy functions are believed to be present. The average molecular weight is controlled by the ratio of M and Q units. This ratio is believed to be about 0.67 for MQ-RESIN POWDER 803 TF.

Silicone polyoxamide PSA composition (S1) was prepared by hot melt compounding the Silicone polyoxamide elastomer with the MQ-RESIN tackifier at a composition of 50 parts/50 parts (by weight). The two resins were fed into a BERSTORFF ZE25 co-rotating twin screw extruder (KraussMaffei Corp., Berstorff Division, Florence, Ky., USA), preset at a temperature of 255° C., at a total feed rate of 10 lbs/hr (4.5 kg/hr). The compounded adhesive was collected, quenched and stored for later use in melt blowing. Melt viscosity was measured by the same technique used for polymer A1. The complex viscosity of silicone polyoxamide PSA S1 in the melt state at 250° C. was 2700 poise.

L1: Release Liner

L1 is a PET Polyester based Fluorosilicone coated Liner, coated on both sides, and was supplied by Loparex LLC (Hammond, Wis., USA).

Fiber Diameter Measurements

After each nonwoven web of the Examples (below) was prepared, its average fiber diameter was measured as follows: For each specimen, images were collected on a NIKON OPTIPHOT-2-POL optical microscope (Nikon Instruments, Inc., Melville, N.Y., USA) using a 5× objective to obtain best depth of focus. Total magnification was 50×. Transmitted polarized light was used to maximize contrast of the fibers in the focal plane. Images of four fields from each specimen were collected. Calibration of the microscope's 5× objective was made against a Leitz stage micrometer. Three separate measurements were made against the micrometer. All were within about 0.6% of the expected value of the calibration standard. Images were collected and analyzed using IMAGE-PRO PLUS software (Media Cybernetics Inc., Bethesda, Md., USA). The calibration for the Nikon 5× objective was selected and 10 measurements of fiber diameter were made manually for each of the four field images. Only fibers that were in focus and possessing sharp edge contrast were measured. The average of the 40 measurements was reported.

Moisture Vapor Transmission Rate (MVTR)

Nonwoven web specimens from some Examples were tested for MVTR, which was evaluated in a manner analogous to that described in ASTM E 96-80, at 40° C. Results are expressed in grams transmitted per square meter per day ($g/m^2/24$ hr).

Examples 1-7

Nonwoven Adhesive Webs

Example 1

Nonwoven web (NW1) was cast such that its fibers were made entirely of the silicone polyoxamide adhesive (S1). The fibers thus had a single layer construction. NW1 was prepared by a melt blowing process, as described in U.S. Pat. Nos. 5,238,733 and 6,083,856, except that specific process conditions such as temperatures and throughputs were set as indicated herein. S1 was cut into small chunks, approximately 1 inch×1 inch×3 inches (2.5 cm×2.5 cm×7.6 cm) in size, using a hot knife. A BONNOT feeder (Bonnot Co., Uniontown, Ohio, USA) was used to feed S1 chunks at a controlled feed rate of 8.0 lbs/hr (3.6 kg/hr) and at melt temperature of 240° C. The melt stream was conveyed to a die, which was maintained at a temperature of 240° C. across the die length. A hot air stream at 300° C., at a flow-rate adjusted to correspond to a 7 psi (48 kPa) pressure drop, was passed through the die manifold to attenuate the exiting melt from the die orifices into continuous fibers, which were collected as randomly oriented fibrous web on the release liner (L1) supported on a drum collector. The distance from die to collector was fixed at 7 inches (18 cm). The speed of the collector was adjusted to 1.2 ft/min (37 cm/min) in order to obtain a basis weight for the web of 75 $g/m^2$. The measured average diameter for the fibers of this web was 37 microns. A nonwoven web specimen of Example 1 had an MVTR of 8490 $g/m^2/24$ hr.

Example 2

Nonwoven web (NW2) was cast such that its fibers had a three-layered construction in which the Silicone polyoxamide adhesive (S1) constituted the outer layers and a hot melt acrylate adhesive (A1) constituted the central (e.g. core) layer. The ratio of the sum of both outer layers to central layer was 80/20 by weight. NW2 was prepared similar to the process described in Example 1, except that the flow rate of the Silicone polyoxamide adhesive (S1) was 6.4 lbs/hr (2.9 kg/hr), and A1 was heated at 200° C. and pumped at the rate of 1.6 lbs/hr (0.73 kg/hr) using a twin screw extruder, and fed into the feedblock. Basis weight of the resulting web was 78 $g/m^2$. The measured average diameter for the fibers of this web was 31 microns.

Example 3

Nonwoven web (NW3) was made as NW2 except that the ratio of the sum of both outer layers to central layer was 60/40 by weight. The flow rates of S1 and A1 were 4.8 lbs/rh (2.2 kg/hr) and 3.2 lbs/hr (1.5 kg/hr), respectively. Basis weight of the resulting web was 78 $g/m^2$. The measured average diameter for the fibers of this web was 34 microns.

Example 4

Nonwoven web (NW4) was made as NW2 except that the ratio of the sum of both outer layers to central layer was 40/60 by weight. The flow rates of S1 and A1 were 3.2 lbs/hr (1.5 kg/hr) and 4.8 lbs/hr (2.2 kg/hr), respectively. Basis weight of the resulting web was 78 $g/m^2$. The measured average diameter for the fibers of this web was 23 microns. A nonwoven web specimen of Example 4 had an MVTR of 8700 $g/m^2/24$ h.

Example 5

Nonwoven web (NW5) was made as NW2 except that the ratio of the sum of both outer layers to central layer was 20/80 by weight. The flow rates of S1 and A1 were 1.6 lbs/hr (0.73 kg/hr) and 6.4 lbs/hr (2.9 kg/hr), respectively. Basis weight of the resulting web was 78 $g/m^2$. The measured average diameter for the fibers of this web was 21 microns.

Example 6

Nonwoven web (NW6) was similar to NW2 except that the Polyolefin Blend (P1) was used in the central layer. The mixture of pellets was fed to the extruder at a controlled rate through a hopper. The ratio of the sum of both outer layers to central layer was 90/10 by weight. Flow rates of S1 and P1 were 7.26 lbs/hr (3.29 kg/hr) and 0.74 lbs/hr (0.34 kg/hr), respectively. Basis weight of the resulting web was 80 $g/m^2$.

The measured average diameter for the fibers of this web was 13 microns.

Example 7

Nonwoven web (NW7) was made as NW6 except that the ratio of the sum of both outer layers to central layer was 80/20 by weight. Flow rates of S1 and P1 were 6.4 lbs/hr (2.9 kg/hr) and 1.6 lbs/hr (0.73 kg/hr), respectively. Basis weight of the resulting web was 80 g/m². The measured average diameter for the fibers of this web was 12 microns.

Adhesive Property Measurements

90° Angle Peel Adhesion Strength Test

Peel adhesion strength was measured at a 90° angle using an IMASS SP-200 slip/peel tester (IMASS, Inc., Accord, Mass., USA) at a peel rate of 305 mm/minute (12 inches/minute) using the procedure described in ASTM International standard, D3330, Method F. Specimens of the nonwoven webs of Examples 1-7 were each laminated onto primed polyester backing (HOSTAPHAN 3SAB PET film, Mitsubishi Polyester Film Inc., Greer, S.C., USA) to make adhesive tapes, and these were stored at constant temperature and humidity for 24 hours. Test panels were prepared by wiping polypropylene panels with a tissue wetted with isopropanol using heavy hand pressure. The panels were wiped 8 to 10 times. This procedure was then repeated two more times with fresh tissues wetted with isopropanol. Each cleaned panel was allowed to dry. For each of the products of Examples 1-7, the laminated adhesive tape was cut into strips measuring 1.27 cm×20 cm (½ in.×8 in.). For each test, a tape strip was rolled down onto a cleaned panel with a 2.0 kg (4.5 lb.) rubber roller using 2 passes. The prepared test specimens were stored at 23° C./50% RH for 24 hours before testing. Two specimens were tested for each Example and the two results were averaged. The peel adhesion strength values were expressed in oz/in and g/in. The failure mode was clean adhesive peel in all cases. Table 1 contains the peel data for the adhesive tapes made from the Examples.

Shear Holding Power Test

Shear Holding Power or Static Shear Strength was evaluated at 23° C./50% RH (relative humidity) using a 500 g load. Tape test specimens, made as previously described, measuring 5.08 cm×15.24 cm (2 in.×6 in.), were adhered to 1.5 inch by 2 inch (3.81 cm×5.08 cm) stainless steel (SS) panels. These panels had been previously cleaned using the same method as that used to clean the polypropylene panels for the peel adhesion test. Each tape was applied so as to overlap the panel by 5.08 cm×2.54 cm (2 in ×1 in.), and the strip was folded over itself on the adhesive side, and then folded again. A hook was hung in the second fold and secured by stapling the tape above the hook. The weight was attached to the hook and the panel was hung in a 23° C./50% RH room. The time to failure in minutes was recorded. If no failure was observed after 10,000 minutes, the test was stopped and a value of 10,000+ minutes was recorded. The mode of failure was cohesive in each sample that failed.

Modified Peel Strength Measurement Test

A modified peel test method was also used. The method was similar to a T-peel as typically performed in a tensile tester, and is described in US Published Patent Application No. 2010/0121304 A1, "Multifunctional acrylate skin adhesive compositions", paragraphs [0033]-[0036]. The peel substrate was a flexible polyethylene sheet. Peel strength was reported in gram per inch width (g/in). For each test, an adhesive tape strip specimen, prepared as already described, was attached to the polyethylene substrate. For each material tested, two specimens were prepared, and the two were held for two different times: 15 min (referred to as T0) and 24 hr (referred to as T24). Table 2 reports the peel strengths at T0 and T24, and also the ratio of peel strengths (T24/T0) for each sample. Thus, a higher T24/T0 ratio represents a greater "adhesion build" over time.

TABLE 1

Peel Strength and Shear Holding Power

| Example Number | Fiber Construction | Basis weight [g/m²] | 90° Peel Strength RT, PP, 1 Kg 12"/min [oz/in] | [g/in] | Shear Holding Power RT, 500 g [min] |
|---|---|---|---|---|---|
| 1 | Single | 75 | 11.6 | 343 | 10,000+ |
| 2 | Multi-component | 78 | 8.7 | 258 | 10,000+ |
| 3 | Multi-component | 78 | 10.2 | 301 | 362 |
| 4 | Multi-component | 78 | 4.1 | 122 | 39 |
| 5 | Multi-component | 78 | 8 | 236 | 31 |
| 6 | Multi-component | 80 | 6.2 | 185 | 10,000+ |
| 7 | Multi-component | 80 | 9.6 | 285 | 10,000+ |

Results shown in Table 1 indicate that Shear Holding Power is very high for the single-layer silicone polyoxamide materials of Example 1, very high for the three-layer materials tested containing polyolefin central layers, and continuously adjustable, from quite low to very high, for the three-layer materials having acrylic central layers, as the percentage of the silicone polyoxamide outer layers material rises. Shear holding power of an adhesive may be desirable for medical adhesives that are used for holding medical devices, such as catheter tubes, absorbent pads, electrodes, and the like.

TABLE 2

Modified Peel strength test results at T0 and at T24

| Example Number | Fiber Construction | Basis weight [g/m²] | Modified Peel Test | | T24/T0 Ratio |
|---|---|---|---|---|---|
| | | | T0 [g/in] | T24 [g/in] | |
| 1 | Single | 75 | 109.1 | 137.3 | 1.26 |
| 2 | Multi-component | 78 | 143.1 | 220.4 | 1.54 |
| 3 | Multi-component | 78 | 256.7 | 402.0 | 1.57 |
| 4 | Multi-component | 78 | 149.8 | 558.3 | 3.73 |
| 5 | Multi-component | 78 | 147.7 | 556.6 | 3.77 |

Results shown in Table 2 indicate that the nonwovens made of fibers having large amounts of the silicone polyoxamide polymer, including the single-layer Example 1, exhibit much lower adhesion build over time. This was a surprising result. For some applications, such as adhesion to skin, it is desired to have a low adhesion build. Thus, the adhesive, when applied on skin, can be left for a long period of time and yet be removed with little pain.

Examples 6-8 were prepared by laminating the fibrous adhesive web of Example 3 onto a polyester nonwoven backing (available under tradename of Sontara® from Dupont™, Wilmington, Del.) using a heat laminator set at 70° C., followed by covering the adhesive with a release liner L1. In order to keep the sample flat for antimicrobial deposition, a PET tape was adhered to the top side of the polyester nonwoven backing. The tape was Scotch® Transparent packaging tape from 3M Company, St. Paul, Minn.

The liner was temporarily removed to coat on the antimicrobial compositions. Coating was done using a computerized ink jet X-Y printer according to Example 1 of US 2006/0034899 at a setting of 100% coverage. The antimicrobial was coated in a dot pattern having an average dot size of about 40 microns in diameter and an average dot spacing of 1 dot per 40,000 square microns of pressure sensitive adhesive web. A fluorescent additive was added to the sample such that microscopy could be used to confirm that the antimicrobial composition had successfully been printed. After coating the sample was allowed to dry for 15 minutes before reapplying the liner to the coated adhesive. The sample was still adhesive to the skin.

| Component | Chemical Name | Supplier | Ex. 6 | Ex. 7 | Ex. 8 |
|---|---|---|---|---|---|
| Capmul PG-8 | propylene glycol monocaprylate | Abitec, Columbus OH | 20 | | |
| Mandelic acid | | Sigma Aldrich, Milwaukee, WI | 5 | | |
| Complemix (DOSS) | docusate sodium | Cytec Ind. Woodland Park, NJ | 5 | | |
| CHG (20%) | chlorhexidine digluconate | Xttrium Labs, Mt. Prospect, IL | | 50 | 50 |
| Crodaphos SG | PPG-5 ceteth-10 phosphate | Croda USA, Parsippany NJ | | | 5 |
| Fluoroscein | | Sigma Aldrich, Milwaukee, WI | 0.1 | | |
| IPA | isopropyl alcohol | Sigma Aldrich, Milwaukee, WI | 69.9 | | |
| water | deionized water | | | | 40 |
| total | | | 100 | 50 | 95 |

The antimicrobial activity was measured using a direct time kill method which is described below and is based on ASTM E2315-03 (reapproved 2008).

A 60-minute time kill study was performed as follows:

A 1.9 cm diameter sample was cut using a die that was decontaminated in 70% isopropyl alcohol/water. The adhesive liner was removed and the sample disks were placed on sterile glass cover slips in a petri dish adhesive side up. A suspension of Staphylococcus aureus (MRSA, ATCC #25923) was prepared at a concentration of $1\times10^8$ CFU (colony forming units) per milliliter (mL) in phosphate buffered water (pbw) using a 0.5 McFarland Equivalence Turbidity Standard. Using an Eppendorf pipette, 50 μL of this suspension was transferred as 15-16 separate droplets to the adhesive. Duplicate disks were tested. The average inoculums was 6.94 log of bacteria. These inoculated specimens were then incubated at (35° C.) for 60 minutes. After incubation, the specimens were placed in 20 mL of neutralizing buffer (Dey Engley neutralizing broth, Sigma Aldrich, Milwaukee, Wis.) and sonicated for one minute followed by vortexing vigorously for two minutes. Portions of the resulting solution were serially diluted with phosphate buffered water. The initial solution and dilutions were each plated in tryptic soy agar (TSA). Plates were incubated for 41 hours at 35 C, removed and colony forming units (CFUs) were counted manually. CFUs from each sample were calculated base on the dilution plate and the average was calculated. The average was converted to a Log 10 value. Log reduction was calculated by subtracting the Log 10 value for the sample from the control.

The antimicrobial results are shown below:

| | 6 | 7 | 8 | Control - no antimicrobial |
|---|---|---|---|---|
| Microbial Reduction % | 41.11563 | 85.20892 | 93.54346 | 0 |
| Microbial reduction (log) | 0.23 | 0.83 | 1.19 | 0 |

The results indicate that the printed nonwoven adhesive exhibits antimicrobial properties.

What is claimed is:

1. A multi-component fiber comprising a core and outer layer, wherein at least a portion of the outer layer comprises a first melt processable composition comprising a polydiorganosiloxane polyoxamide copolymer pressure sensitive adhesive comprising greater than 50 weight percent polydioorganosiloxane and at least a portion of the core comprises a second melt processable polymer that does not comprise a polydiorganosiloxane polymer wherein the polydiorganosiloxane polyoxamide copolymer pressure sensitive adhesive is present at a weight ratio to the second melt processable polymer ranging from 80/20 to 90/10 and the multi-component fiber exhibits a shear holding power at 23° C./50% relative humidity of at least 10,000 minutes with a 500 g weight.

2. The multi-component fiber of claim 1 wherein the first melt processable composition comprises a polydiorganosiloxane polyoxamide comprising at least two repeat units of Formula I:

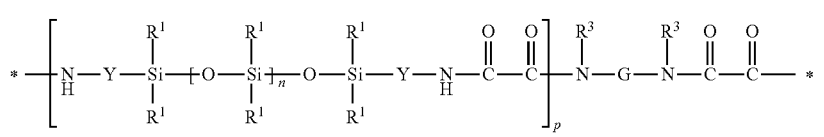

wherein
each $R^1$ is independently an alkyl, haloalkyl, aralkyl, alkenyl, aryl, or aryl substituted with an alkyl, alkoxy, or halo, wherein at least 50 percent of the $R^1$ groups are methyl;
each Y is independently an alkylene, aralkylene, or a combination thereof;
G is a divalent residue equal to a diamine of formula $R^3HN-G-NHR^3$ minus the two $-NHR^3$ groups;
$R^3$ is hydrogen or alkyl or $R^3$ taken together with G and with the nitrogen to which they are both attached forms a heterocyclic group;
n is independently an integer of 40 to 1500; and
p is an integer of 1 to 10; and
an asterisk (*) indicates a site of attachment of the repeat unit to another group in the copolymer.

3. The multi-component fiber of claim 2 wherein each $R^1$ is methyl and $R^3$ is hydrogen.

4. The multi-component fiber of claim 2 wherein the copolymer has a first repeat unit where p is equal to 1 and a second repeat unit where p is at least 2.

5. The multi-component fiber of claim 2 wherein G is an alkylene, heteroalkylene, arylene, aralkylene, polydiorganosiloxane, or a combination thereof.

6. The multi-component fiber of claim 2 wherein Y is an alkylene.

7. The multi-component fiber of claim 2 wherein n is an integer of 100 to 500.

8. The multi-component fiber of claim 2 wherein the first melt processable composition is a pressure sensitive adhesive comprising about 40 wt-% to 60 wt-% of silicate tackifying resin.

9. The multi-component fiber of claim 8 wherein the tackifying resin is present in an amount of at least 10 wt-% of the total multi-component fiber.

10. The multi-component fiber of claim 1 wherein the first melt processable composition has a complex viscosity ranging from 500 to 5000 poise at a temperature ranging from 200° C. to 300° C.

11. The multi-component fiber of claim 10 wherein the second melt processable polymer has a complex viscosity ranging from 500 to 5000 poise at a temperature ranging from 180° C. to 300° C.

12. The multi-component fiber of claim 1 wherein the second polymer is selected from an acrylic polymer, polyolefin polymer, a styrenic block copolymer, or a mixture thereof.

13. The multi-component fiber of claim 12 wherein the second polymer is an acrylate pressure sensitive adhesive.

14. A nonwoven web comprising the multi-component fiber of claim 1.

15. The nonwoven web of claim 14 wherein the web is a pressure sensitive adhesive having a 90 degree peel strength to polypropylene ranging from 100 to 500 g/inch as measured according to D-3330-87.

16. A medical article comprising a backing and a nonwoven web according to claim 15.

17. The medical article of claim 16 wherein the article is selected from the group consisting of tapes, wound dressings, and incise drapes.

18. The nonwoven web of claim 14 wherein the web has an MVTR of at least 1000 g/m$^2$/24 h.

19. The nonwoven web of claim 14 wherein the web further comprises an antimicrobial.

20. A method of making multi-component microfibers comprising:
   providing a first melt processable composition comprising a polydiorganosiloxane polyoxamide copolymer pressure sensitive adhesive comprising greater than 50 weight percent polydioorganosiloxane wherein the composition has a complex viscosity ranging from 500 to 5000 poise at a temperature ranging from 200° C. to 300° C. and a shear rate of 1 hertz; and
   providing a second melt processable composition that does not comprise a polydiorganosiloxane polymer; and
   melt-blowing the first and second melt processable composition to form multi-component fibers wherein the polydiorganosiloxane polyoxamide copolymer pressure sensitive adhesive is present at a weight ratio to the second melt processable polymer ranging from 80/20 to 90/10 and the multi-component fibers exhibits a shear holding power at 23° C./50% relative humidity of at least 10,000 minutes with a 500 g weight.

* * * * *

UNITED STATES PATENT AND TRADEMARK OFFICE
CERTIFICATE OF CORRECTION

PATENT NO. : 9,617,668 B2
APPLICATION NO. : 14/233174
DATED : April 11, 2017
INVENTOR(S) : Chatterjee et al.

Page 1 of 2

It is certified that error appears in the above-identified patent and that said Letters Patent is hereby corrected as shown below:

On the Title Page

Column 1, item [65] Prior Publication Data
Insert -- US 61/522,485 Aug. 11, 2011 --.

In the Specification

Column 3
Line 67, after "peel)" insert -- . --.

Column 4
Line 6, delete "tackifer" and insert -- tackifier --, therefor.

Column 10
Line 37, delete "510$_{4/2}$" and insert -- SiO$_{4/2}$ --, therefor.
Line 37, delete "R'SiO$_{312}$" and insert -- R'SiO$_{3/2}$ --, therefor.

Column 12
Line 50, delete "methocy" and insert -- methoxy --, therefor.

Column 13
Line 36, delete "temepratue" and insert -- temperature --, therefor.

Column 14
Line 54, after "m$^2$" insert -- . --.

Column 16
Line 16, delete "(C2-C8)hydroxycarboxylic" and insert -- (C2-C8) hydroxycarboxylic --, therefor.
Line 18, delete "(C2-C8)hydroxycarboxylic" and insert -- (C2-C8) hydroxycarboxylic --, therefor.
Line 20, delete "(C2-C8)hydroxycarboxylic" and insert -- (C2-C8) hydroxycarboxylic --, therefor.

Signed and Sealed this
Sixth Day of February, 2018

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,617,668 B2

Column 17
Line 11, delete "sufadiazine." and insert -- sulfadiazine. --, therefor.
Line 19, delete "polyethyoxylated" and insert -- polyethoxylated --, therefor.
Line 26-27, delete "(phloro, lucinol" and insert -- (phloroglucinol --, therefor.
Line 32, delete "chamomille;" and insert -- chamomile; --, therefor.
Line 42, delete "patchouly" and insert -- patchouli --, therefor.
Line 42-43, delete "PLANSERVATIVE" and insert -- PLANTSERVATIVE --, therefor.

Column 18
Line 31, after "RESIN" insert -- . --.

Column 23
Line 28, delete "Fluoroscein" and insert -- Fluorescein --, therefor.

Column 24
Line 2, delete "35 C," and insert -- 35° C. --, therefor.
Line 4, delete "base" and insert -- based --, therefor.

In the Claims

Column 24
Line 27-28, Claim 1, delete "polydioorganosiloxane" and insert -- polydiorganosiloxane --, therefor.

Column 26
Line 18, Claim 20, delete "polydioorganosiloxane" and insert -- polydiorganosiloxane --, therefor.
Line 27, Claim 20, delete "fibers" and insert -- fibers; --, therefor.